United States Patent
Langley et al.

(10) Patent No.: US 7,699,815 B2
(45) Date of Patent: *Apr. 20, 2010

(54) DRIVE MECHANISM FOR AN INJECTION DEVICE

(75) Inventors: Christopher Nigel Langley, Leamington Spa (GB); Shane Alistair Day, Warwick (GB); Robert Frederick Veasey, Leamington Spa (GB); Robert Woolston, Warwick (GB)

(73) Assignee: DCA Design International Limited, Warwick (GB)

( * ) Notice: Subject to any disclaimer, the term of this patent is extended or adjusted under 35 U.S.C. 154(b) by 11 days.

This patent is subject to a terminal disclaimer.

(21) Appl. No.: 10/433,782

(22) PCT Filed: Dec. 21, 2001

(86) PCT No.: PCT/GB01/05705

§ 371 (c)(1),
(2), (4) Date: Jun. 6, 2003

(87) PCT Pub. No.: WO02/051472

PCT Pub. Date: Jul. 4, 2002

(65) Prior Publication Data
US 2004/0054329 A1    Mar. 18, 2004

(30) Foreign Application Priority Data
Dec. 22, 2000   (GB) .................... 0031466.6

(51) Int. Cl.
A61M 5/00 (2006.01)
A61M 37/00 (2006.01)

(52) U.S. Cl. .................. 604/209; 604/131

(58) Field of Classification Search .............. 604/131, 604/151, 155, 207–211
See application file for complete search history.

(56) References Cited

U.S. PATENT DOCUMENTS

| 2,866,910 A | * | 12/1958 | Bentley .................. 310/20 |
| 4,619,646 A | | 10/1986 | Fernandez-Tresguerres Hernandez et al. |
| 4,749,109 A | | 6/1988 | Kamen |
| 4,921,487 A | * | 5/1990 | Buffet et al. .............. 604/135 |

(Continued)

FOREIGN PATENT DOCUMENTS

GB    2 094 628 A    9/1982

(Continued)

*Primary Examiner*—Kevin C Sirmons
*Assistant Examiner*—Andrew M Gilbert
(74) *Attorney, Agent, or Firm*—Oliff & Berridge, PLC.

(57) ABSTRACT

A drive mechanism for an injection device is disclosed in which piston means are selectively driven to expel medicament from within a medicament cartridge. The drive mechanism comprises a drive means associated with a first ratchet member, a second ratchet member associated with the piston means, a housing, the first ratchet member and the second ratchet member being disposed within the housing. The second ratchet member being biased by biasing means toward the first ratchet member. The drive means is actuable reciprocally to drive the first ratchet member in a first angular direction such that the first ratchet member drives the second ratchet member along its longitudinal axis against the biasing means along at least a part of its movement and subsequently drives the first ratchet member and the second ratchet member together in a second angular direction thereby to drive the piston means.

5 Claims, 3 Drawing Sheets

U.S. PATENT DOCUMENTS

| | | | |
|---|---|---|---|
| 4,955,868 A * | 9/1990 | Klein | 604/198 |
| 5,219,099 A | 6/1993 | Spence et al. | |
| 5,448,117 A * | 9/1995 | Elliott | 310/49 R |
| 5,626,566 A * | 5/1997 | Petersen et al. | 604/208 |
| 5,820,602 A | 10/1998 | Kovelman et al. | |
| 5,823,998 A * | 10/1998 | Yamagata | 604/131 |
| 6,042,571 A * | 3/2000 | Hjertman et al. | 604/208 |
| 6,379,337 B1 * | 4/2002 | Mohammad | 604/195 |
| 6,623,459 B1 * | 9/2003 | Doyle | 604/197 |
| 6,716,198 B2 * | 4/2004 | Larsen | 604/207 |
| 6,969,370 B2 * | 11/2005 | Langley et al. | 604/131 |
| 6,972,007 B2 * | 12/2005 | Geiser et al. | 604/211 |

FOREIGN PATENT DOCUMENTS

| | | |
|---|---|---|
| WO | WO 97/36623 | * 10/1997 |
| WO | WO 00/25844 | 5/2000 |
| WO | WO 00/47254 | 8/2000 |

* cited by examiner

DRIVE MECHANISM FOR AN INJECTION DEVICE

This is a U.S. National Stage of PCT/GB2001/05705 filed Dec. 21, 2001, which claims priority to GB 0031466.6, filed Dec. 22, 2000, the subject matter of which is incorporated herein in its entirety by reference thereto.

The present invention relates to improvements in an injection device, and in particular to improvements in a portable injection device for dispensing controlled quantities of a medicament.

Typically such injection devices are used by those suffering from diabetes to administer a dose of insulin or insulin-type medicine to themselves. It will be understood that such injection devices are suitable for the injection of other medicines.

At one time, such doses were administered by use of a disposable syringe; the syringe first being filled from a separate phial or other container and then used to inject the dose. However, there were a number of difficulties in such an arrangement. In particular, such an arrangement was not suitable for the infirm. For others, the social stigma associated with such syringes made their public use problematic.

To overcome these difficulties a number of so-called pen-type injectors have been developed. These devices are small, being capable of being carried in a jacket pocket or the like and allow a number of doses to be obtained from a cartridge or ampoule contained within the injector. The present invention has particular application to such pen-type injectors.

While such pen-type injectors are a considerable improvement upon disposable hypodermic syringes, problems nevertheless remain.

In particular when considering the design of a drive system for a pen-type injector, there are a number of, sometimes, conflicting technical requirements. The drive system must be accurate and reliable, and at the same time compact and efficient. The drive system must be reliable and robust; being able to function for the life of the product. The drive system must also be intrinsically fail-safe.

It is an advantage of the present invention that it eliminates, or at least substantially reduces such problems. The present invention also provides for improved ease of use and improved interaction with a user.

The invention will now be described, by way of example only, with reference to the accompanying drawings; in which.

Figures 1, 2:
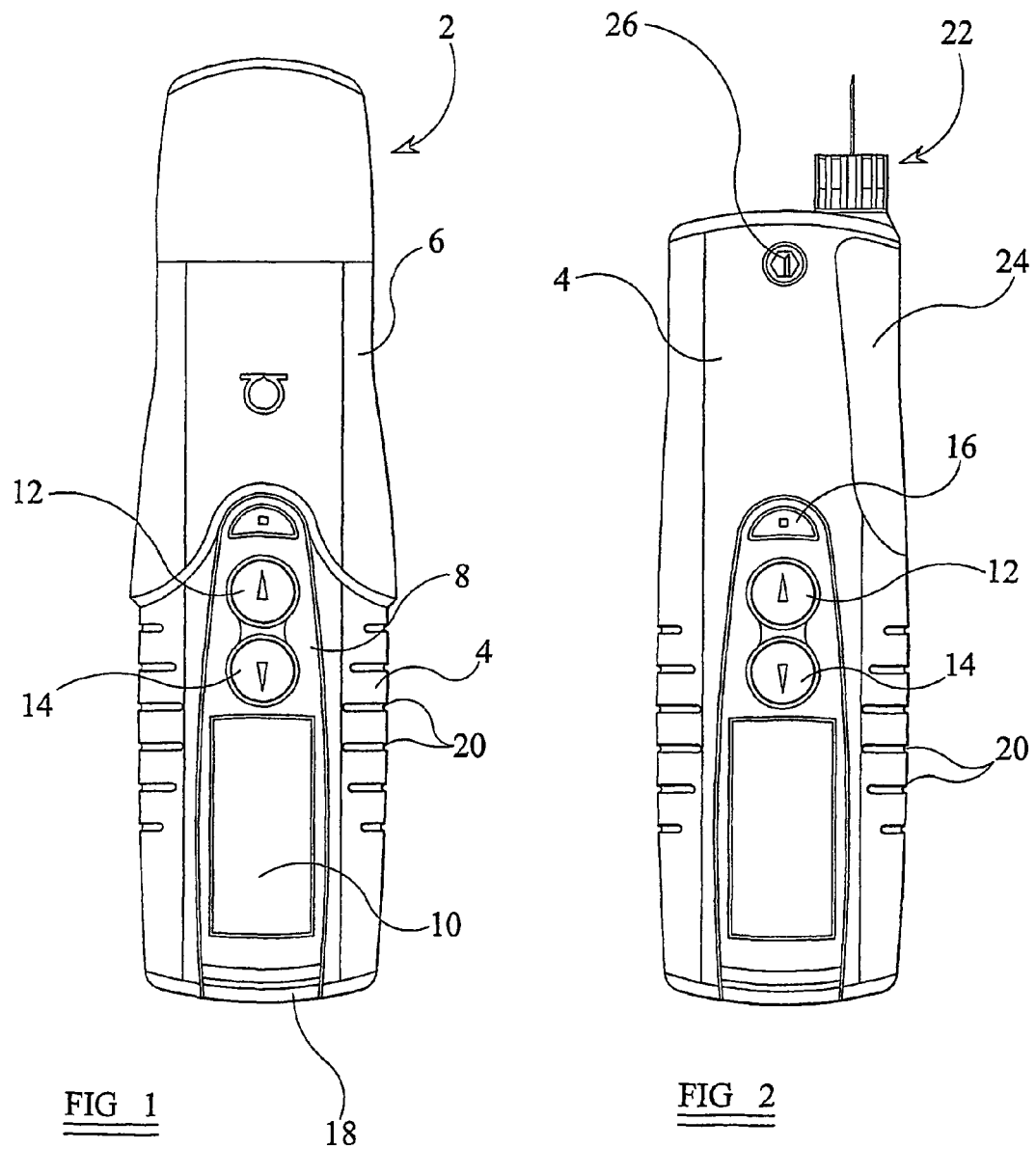
FIG. 1 shows a plan view of a pen-type injector in accordance with the present invention.
FIG. 2 shows a similar view to FIG. 1 with an end cap of the injector omitted.
Figure 3:
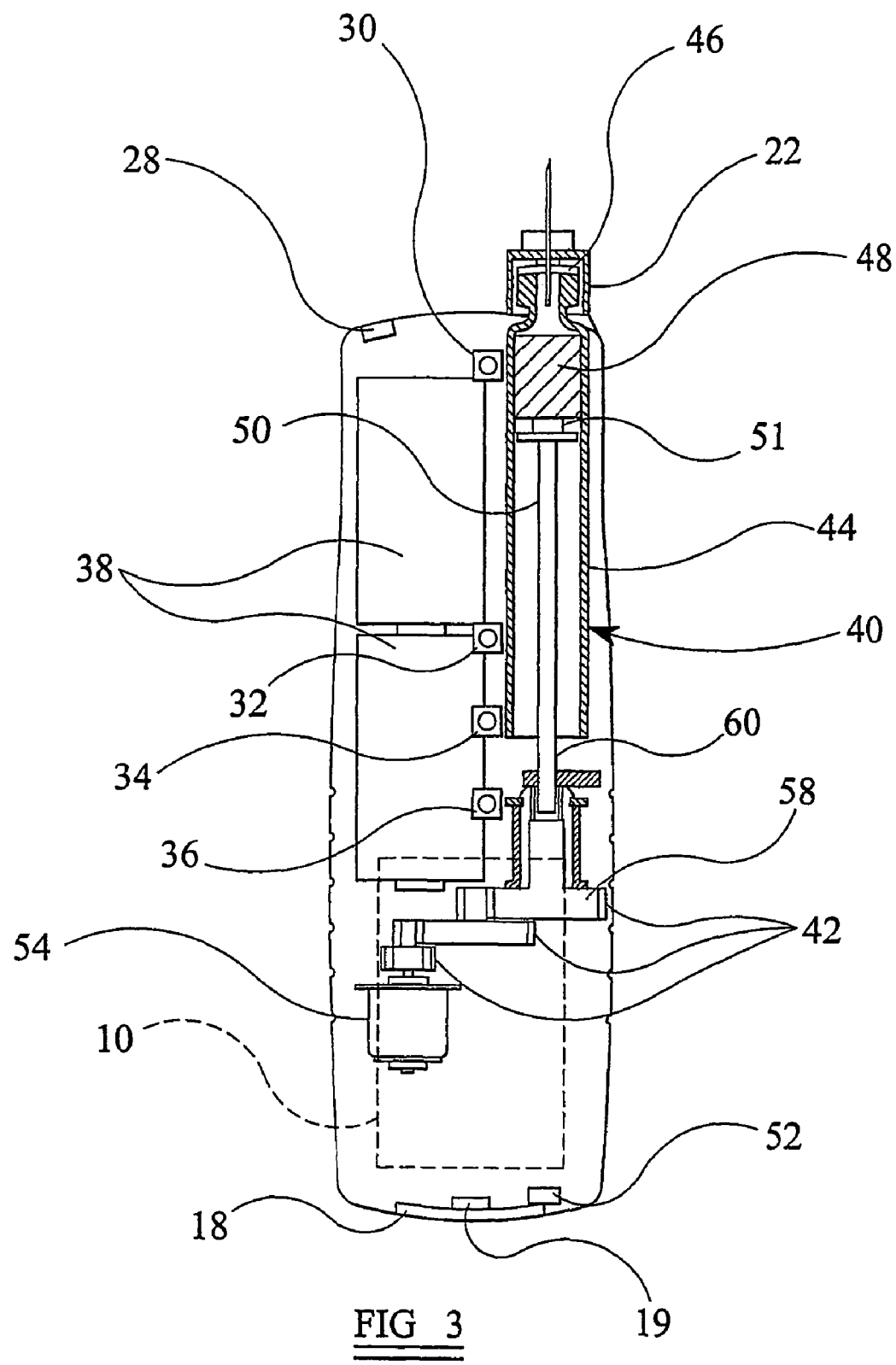
FIG. 3 shows a cross-sectional view of the injector of FIGS. 1 and 2.

Referring first to FIGS. 1 to 3, there can be seen a pen-type injector 2 in accordance with the present invention. The injector 2 comprises a main housing 4 to which is releasably secured an end cap or cover 6.

At a first end of the main housing 4 there is provided a control panel region 8. This region includes a display panel 10, typically a LCD display, and a first dose button 12 and a second dose button 14, the first and second dose buttons being operated to increase or decrease a dose of medicament to be delivered. The control panel region 10 in the illustrated embodiment also includes an arm button 16.

At the first end of the main housing there is also provided a dispense button 18. Preferably, when not depressed, the dispense button 18 is flush with the main housing 4.

Along a longitudinal axis of the injector 2, to each side of the control panel region 10 are provided a number of grooves or recesses 20. These aid in the gripping of the injector 2 by a user.

At a second end of the main housing 4 a needle unit 22 is releasably secured to the main housing. The second end of the main housing 4 is also provided with a shaped portion 24.

In use a cartridge 40 or ampoule of medicament is stored in the housing 4 behind the shaped portion 24. For preference, the shaped portion is transparent to permit the cartridge 40 to be seen by a user.

A primer button 26 is also provided on the second end of the housing 4. It will be understood that when the end cap 6 is in place over the second end of the housing, it will not be possible inadvertently to depress the primer button 26 or to be pricked by the needle unit 22. A cover detection switch 28 may also be included at the second end of the main housing 4 to detect whether the end cap or cover 6 is in place or not.

In FIG. 3, there can be seen a priming contact 30, an arm contact 32, a first dose contact 34 and a second dose contact 36 corresponding to the respective buttons. A dispense contact 19 corresponding to the dispense button 18 is also shown.

With reference to FIG. 3 it may be seen that there is provided a suitable location for a power source 38 such as a battery or batteries. There is also a suitable region in which a cartridge 40 or ampoule of medicament is to be located. This region may be accessed by way of the removable shaped portion 24 of the main housing 4 to allow for replacement of the cartridge 40 or ampoule as required by the user. An alternative cartridge access means is disclosed in relation to FIGS. 16 to 23.

In a third region of the main housing 4 there is provided a drive mechanism 42 which operates from the power source 38 and acts upon the cartridge 40 or ampoule of medicament.

The cartridge 40 or ampoule comprises a container 44 or sleeve closed at one end by a cover 46 at a head end thereof, and sealed at the other by a movable bung 48 or stopper. When in position, the needle unit 22 pierces the cover 46 and movement of the bung 48 towards the cover 46 will cause the medicament contained within the cartridge 40 or ampoule to be expelled. The cartridge may be a 3 ml cartridge in accordance with ISO/FDIS 11608 Part 3, or any other suitable cartridge to suit the injector.

Movement of the bung 48 or stopper is caused by movement of a piston or plunger 50 forming a part of the drive mechanism 42. The piston or plunger 50 is movable between a first fully withdrawn position (not shown) which allows for the replacement of the cartridge 40 or ampoule and a second fully extended portion in which as much medicament as possible has been expelled from the cartridge 40 or ampoule. An end stop switch 52 may be provided in the main housing 4 to detect when the piston 50 is in the fully withdrawn position. Tripping of the switch end stop 52 may release a catch or other fastening device to allow access to the main housing 4 for replacement of the cartridge 40.

The drive mechanism 42 is operated by a motor 54 under the control of an electronic control unit (not shown). The motor 54 should be reversible in order to allow the piston 50 to be moved between the first and second positions. In FIG. 3, the motor 54 can be seen to drive the piston 50 by way of a gear train 42, such that rotation of a third rotor 58 causes the piston 50 to be moved in relation to the third rotor 58.

Preferably, the user can feel the vibration of the motor 54 and the associated drive mechanism 42 and/or hear them in operation. In this way an added degree of confidence in the fact of the operation of the injector 2 is provided to the user.

The functionality of a pen-type injector in accordance with the present invention will now be described, in particular with reference to FIGS. 1, 2 and 3.

The injector 2 is provided with an electronic control unit. The electronic control unit is coupled both to the drive mechanism and a user interface. The user interface includes the display panel 10 as well as the user operable buttons (and associated contacts). The electronic control unit is microprocessor based. Either volatile or non-volatile memory may be used for storage of 'dose history' and patient specific information.

The electronic control unit is preferably powered from the injector power source 38.

The injector 2 preferably also includes a port for communication between the electronic control unit and an external apparatus such as a personal computer.

The injector 2 also has a priming detection facility, (such as a tilt switch or accelerometer) to identify when the injector 2 is inverted. On detection of an inverted position (needle up) the injector 2 will automatically change state to be ready for priming. Priming may be initiated by depression of the primer button 26 to cause a fixed small dispense action. The electronic control unit may cause a speaker to sound when the primer button 26 is depressed.

The primer button 26 is inactive at all other times. When the primer button 26 is active, all other buttons in the control panel region are inactive, that is those buttons which are to be used to set or dispense a dose.

The electronic control unit may cause a speaker to sound when the arm button 16 is depressed for a sufficient period of time to provide audible feedback for the user.

The function of the arm button 16 is to make the dispense button 18 active. The arm button is preferably held down for a predetermined period of time before the injector 2 becomes armed. The armed status may additionally be shown on the display panel 10. The functionality of the arm button is preferably linked to the cover detection switch 28 such that the arm button 16 will only function to arm the injector 2 when the cover 6 is not present.

Additionally, in a preferred embodiment, a clock within the electronic control unit will detect whether the dispense button 18 has been pressed within a specified time interval following arming of the injector 2. If the dispense button 18 has not been depressed within the specified time interval the electronic control unit will disarm the injector 2. Alternatively, if the arm button is depressed a second time within a predetermined time period by the user, the injector will be disabled.

In an alternative embodiment, the dispense button 18 may function as both a prime button and the dose button. When the priming detector is actuated, by the injector 2 being oriented needle up, the dispense button 18 would change function to that of the prime button of the previous embodiment.

The buttons of the injector 2 are preferably tactile in nature to provide sensory feedback to the user.

Figure 4:
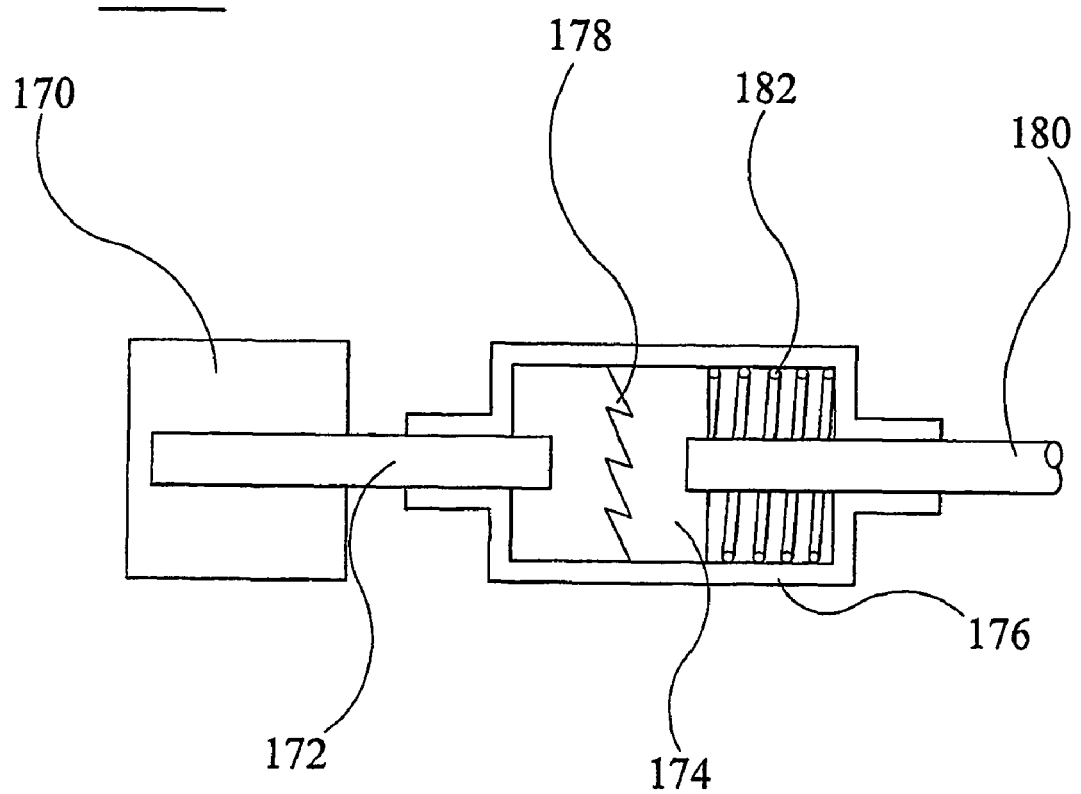
FIG. 4 shows a schematic view of an alternative drive mechanism for use with an injector in accordance with the invention.

In FIG. 4, there is shown a drive means 170 having an output shaft 172. The drive means 170 can be in the form of a rotary solenoid. The rotary solenoid typically converts linear push/pull notion to a few degrees (approx. 15°) of rotary motion by way of a spiral ball race within the solenoid. The output shaft 172 engages a first ratchet member 178. The first ratchet member 178 drives a second ratchet member 174 attached to a shaft of a lead screw. The lead screw will be understood to comprise piston means 180 for the advancement of bung 48 within a medicament cartridge 40 within the context of this description. The first and second ratchet members 178, 174 are located in a housing 176. The second ratchet member 174 is biased towards the first ratchet member 178. The biasing means 182 can be, for example, a helical spring.

On a first stroke of the solenoid, the first ratchet member 178 is caused to rotate. As seen in FIG. 4 the nearmost teeth of the first ratchet member 178 move upwards, thereby pushing the corresponding teeth of the second ratchet member 174 away and against the biassing means. The teeth are disposed angularly about the first and second ratchet members 178,174 to correspond to just less than the angular displacement of the output shaft of the rotary solenoid 170. At the end of the stroke the teeth of the first ratchet member 178 will have indexed to engage the next set of teeth of the second ratchet member 174. On the return stroke of the solenoid 170, the first ratchet member 178 travels in an opposite direction, thereby driving the second ratchet member 174 and the associated shaft 180 of the lead screw.

The invention claimed is:

1. A drive mechanism for an injection device in which piston means are selectively driven to expel medicament from within a medicament cartridge, the drive mechanism comprising:

a drive means associated with a first ratchet member;
a second ratchet member associated with the piston means; and
a housing, wherein
the first ratchet member and the second ratchet member are disposed within the housing,
the second ratchet member being biased by biasing means towards the first ratchet member, in which the drive means is actuable reciprocally to drive the first ratchet member in a first angular direction of rotary motion such that the first ratchet member drives the second ratchet member along its longitudinal axis against the biasing means along at least a part of its movement and subsequently to drive the first ratchet member and the second ratchet member together in a second angular direction thereby to drive the piston means, and
the drive means comprises a rotary solenoid.

2. A drive mechanism according to claim 1, wherein the piston means comprises a lead screw.

3. A drive mechanism according to claim 1, wherein the first ratchet member and the second ratchet member comprise teeth and the first ratchet member drives the second ratchet member along a longitudinal axis of the second ratchet member against the biasing means by pushing the teeth of the second ratchet member away.

4. A drive mechanism according to claim 2, wherein the second ratchet member is attached to a shaft of the lead screw.

5. A drive mechanism according to claim 1, wherein the rotary solenoid has a range of motion of approximately 15°.

* * * * *